United States Patent [19]

Georgiev et al.

[11] Patent Number: 4,730,063

[45] Date of Patent: Mar. 8, 1988

[54] ALKALI METAL 2,5-DIHYDRO-3-ETHOXYCARBONYL-2-[(SUBSTITUTED PHENYL)AMINO]-4-FURANYLOXIDES

[75] Inventors: Vassil S. Georgiev, Rochester; Clyde R. Kinsolving, Fairport; Robert A. Mack, Rochester, all of N.Y.

[73] Assignee: Pennwalt Corportion, Philadelphia, Pa.

[21] Appl. No.: 938,199

[22] Filed: Dec. 5, 1986

[51] Int. Cl.⁴ .......................................... C07D 307/68
[52] U.S. Cl. ...................................................... 549/479
[58] Field of Search ......................................... 549/479

[56] References Cited

U.S. PATENT DOCUMENTS 2,895,956  7/1959  Tuppy ................................ 546/89

OTHER PUBLICATIONS

Tuppy et al., Chemical Abstracts, vol. 51 (1957) 8093e and 8094e.

Primary Examiner—Richard L. Raymond

[57] ABSTRACT

Alkali metal 2,5-dihydro-3-ethoxycarbonyl-2-[(substituted phenyl)amino]-4-furanyloxides are useful as anti-allergy agents.

7 Claims, No Drawings

ALKALI METAL 2,5-DIHYDRO-3-ETHOXYCARBONYL-2-[(SUBSTITUTED PHENYL)AMINO]-4-FURANYLOXIDES

BACKGROUND OF THE INVENTION

A number of 2-(substituted amino)-4,5-dihydro-4-oxo-3-furancarboxylic acid esters are known. Treatment of the esters with a weak base in aqueous media produces the acid salts. Treatment of the esters with a stronger base produces enol salts. These enol salts possess anti-allergy activity.

BRIEF SUMMARY OF THE INVENTION

In accordance with this invention there are provided compounds of the formula:

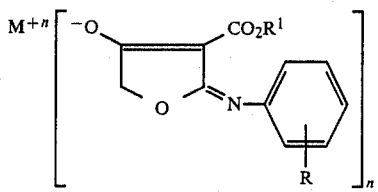

where;
n=1 or 2,
M is an alkali or alkaline earth metal, R is hydrogen, lower alkyl, lower alkoxy, nitro, halogen or acetyl, and $R^1$ is lower alkyl.

DETAILED DESCRIPTION

The alkali metal 2,5-dihydro-3-ethoxycarbonyl-2-[(substituted phenyl)amino]-4-furanyloxides are prepared from the corresponding 4,5-dihydro-4-oxo-2-(phenylamino)-3-furancarboxylic acid esters by treating the latter with a strong base. The acid esters 3 can be prepared as known in the art by a base catalyzed cyclocondensation of an alkyl haloacetoacetate (1) with an appropriate isocyanate (2) as described, for example by Capuano, L. et al., *Chem. Ber.*, 109, pp 212–217 (1976) and illustrated below.

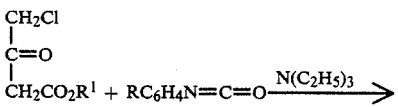

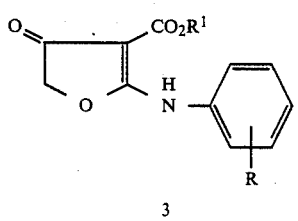

The enol salts are prepared from the corresponding esters 3 by treatment with a sufficient concentration of a strong base such as potassium hydroxide in anhydrous ethanol. Examples of other strong alkali or alkaline earth metal bases which can be used include sodium hydroxide, lithium hydroxide, calcium hydroxide and magnesium hydroxide. Other alcoholic solvents containing from 1 to 4 carbon atoms can be employed, for example, methanol, isopropanol, t-butanol, n-propanol, n-butanol, and i-butanol. The concentration of base solution can range from about 1 to 2 molar and amounts of base solution are added to an alcoholic solution of ester to provide from at least about 1 mmol to 2 mmol of base per mmol of ester.

In the defintions of R and $R^1$, by lower alkyl and lower alkoxy are meant groups containing one to four carbon atoms which can be in a straight or branched chain. By halogen is meant chlorine, bromine, fluorine and iodine, with bromine being preferred.

The following specific, nonlimiting procedures and examples illustrate the preparation of various compounds of the invention.

EXAMPLE 1

Preparation of potassium 2,5-dihydro-3-ethoxycarbonyl-2-(phenylimino)-4-furanyloxide Under nitrogen atmosphere, a solution of potassium hydroxide (5.33 g, 81 mmol) in 50 ml ethanol was added dropwise over a period of 75 min to a stirred solution of 4,5-dihydro-4-oxo-2-phenylamino-3-furancarboxylic acid ethyl ester (3) (20 g, 81 mmol) in 450 ml ethanol, while cooling (ice/water bath). The reaction mixture was stirred at room temperature for 30 min, and then refluxed for another 30 min. The solid precipitate was filtered off while still hot, then rinsed repeatedly with ethanol, followed by ether. After drying, 20.10 grams of the white crystalline salt were obtained. Mp>300° C.

Anal. Calcd. for $C_{13}H_{12}KNO_4$: C, 54.72; H, 4.24; K, 13.70; N, 4.91. Found: C, 54.78; H, 4.09; K, 13.57; N, 5.00.

EXAMPLES 2–6

The following salts were prepared according to the procedure of Example 1 from the corresponding acid esters.

2. potassium 2,5-dihydro-3-ethoxycarbonyl-2-[(3-methylphenyl)imino]-4-furanyloxide.

Anal. Calcd. for $C_{14}H_{14}KNO_4$: C, 56.17; H, 4.71; K, 13.06; N, 4.68. Found: C, 56.04; H, 4.86; K, 13.22; N, 4.66.

3. potassium 2,5-dihydro-3-ethoxycarbonyl-2-[(4-acetylphenyl)imino]-4-furanyloxide.

Anal. Calcd. for $C_{15}H_{14}KNO_5$: C, 55.03; H, 4.31; K, 11.94; N, 4.28. Found: C, 54.89; H, 4.54; K, 11.94; N, 4.24.

4. potassium 2,5-dihydro-3-ethoxycarbonyl-2-[(3-nitrophenyl)imino]-4-furanyloxide.

Anal. Calcd. for $C_{13}H_{11}KN_2O_6$: C, 47.27; H, 3.36; K, 11.84; N, 8.48. Found: C, 47.15; H, 3.66; K, 12.09; N, 8.52.

5. potassium 2,5-dihydro-3-ethoxycarbonyl-2-[(2-methoxyphenyl)imino]-4-furanyloxide.

Anal. Calcd. for $C_{14}H_{14}KNO_5$: C, 53.32; H, 4.47; K, 12.40; N, 4.44. Found: C, 53.33; H, 4.51; K, 12.38; N, 4.42.

6. potassium 2,5-dihydro-3-ethoxycarbonyl-2-[(4-bromophenyl)imino]-4-furanyloxide.

anal. Calcd. for $C_{13}H_{11}BrKNO_4$: C, 42.87; H, 3.04; Br, 21.94; K, 10.73; N, 3.85. Found: C, 42.64; H, 3.12; Br, 21.98; K, 10.98; N, 3.84.

The compounds of Examples 1 to 6 were tested for anti-allergy activity and are active in the rat active anaphylaxis model and/or the rat dermal vascular permeability test (mediator-release model) in that they inhibit mediator release from sensitized rat mast cells and inhibit wheal formation and flare reactions produced in rats by the intradermal injection of the allergic mediators histamine, serotonin or bradykinin.

In the rat active anaphylaxis model, groups consisting of 15-20 male rats are intraperitoneally sensitized on day zero with 500 ug of bovine serum albumin-absorbed alum admixed with $2 \times 10^{10}$ killed *Bordatella pertussis* vaccine organisms. Fourteen days later, the right hind paw is injected subcutaneously with 100 ug of bovine serum albumin one hour post compound administration at a dosage of 100 mg/kg of rat weight intraperitoneally as a 0.85% weight solution in saline. The paw volume is measured using a mercury plethysmometer prior to drug administration and 90 minutes post antigenic challenge. The percent inhibition of edema is calculated as the difference in volume between the control and drug treated groups divided by the control volume times 100. The positive control drug, theophylline (90 mg/kg, po) is included in each assay. Statistical analysis of the data is done using the poolt program.

In the rat dermal vascular permeability test, groups of ten male rats are intraperitoneally or perorally administered either the test compound at a dosage of 100 mg/kg of rat weight as a 0.85% weight solution in saline or the positive reference standard cyproheptadine (1 mg/kg) one hour prior to an intravenous injection of 1 ml of a 0.5% solution of Evan's blue dye into naive animals. Ten minutes later, the animals are challenged by intradermally injecting 0.1 ml of a solution of either serotonin (1 ug/ml), histamine (20 ug/ml) or bradykinin (10 ug/ml) into separate sites on the back. Five minutes following challenge the animals are killed, the skin retracted, and the mean diameter of the blue wheal and flare reactions determined. The percent inhibition of the wheal reaction is calculated as the difference in diameter between the saline control and drug treated groups divided by the control diameter times 100. Statistical analysis of the data is done using the poolt program.

The results of the tests are given in Table I.

TABLE I

| Compound | | | Active Anaphylaxis % Inhibition | % Inhibition of Mediator Release[1] | | |
|---|---|---|---|---|---|---|
| M | R | $R^1$ | | Serotonin | Histamine | Bradykinin |
| K | H | $C_2H_5$ | 49 | 42 | 31 | 51 |
| K | —$CH_3$—3 | $C_2H_5$ | — | 75 | 71 | 70 |
| K | —$COCH_3$—4 | $C_2H_5$ | 56 | 79 | 88 | 86 |
| K | —$NO_2$—3 | $C_2H_5$ | 37 | 45 | 49 | 67 |
| K | —$OCH_3$—2 | $C_2H_5$ | 58 | — | — | — |
| K | —Br—4 | $C_2H_5$ | 38 | 46 | 65 | 69 |

[1]intraperitoneal administration

In addition, when tested for anti-inflammatory activity in the carrageenan-induced rat paw edema assay, potassium 2,5-dihydro-3-ethoxycarbonyl-2-(phenylimino)-4-furanyloxide and potassium 2,5-dihydro-3-(ethoxycarbonyl)-2-[(3-nitrophenyl)imino]-4-furanyloxide, at oral doses of 50 mg/kg, elicited 31 and 28.3% inhibition of edema, respectively.

For pharmaceutical purposes, the compounds can be administered to warm-blooded animals perorally, parenterally or intranasally as active ingredients in customary dosage unit compositions. These dosage unit compositions contain the active ingredient and at least one inert pharmaceutical carrier. Dosage unit forms can include tablets, capsules, solutions, suspensions, aerosols, and parenteral compositions such as intramuscular, intravenous or intradermal preparations. Sustained release dosage forms are also contemplated where the active ingredient is bound to an ion exchange resin which, optionally, can be coated with a diffusion barrier coating to modify the release properties of the resin.

The quantity of active ingredient administered in such dosage forms can vary over a wide range depending upon the mode of administration, the size and weight of the patient and whether the nature of the treatment is prophylactic or therapeutic in nature. In general, dosage unit forms contain from about 5 mg to 250 mg of the active ingredient and, in man, the dosage is administered from 1 to 4 times daily. The total daily dosage will be from about 5 mg to 1000 mg although lower and higher amounts can be used. A preferred total daily dose would be from 10 mg to 100 mg of active ingredient.

Pharmaceutical carriers or excipients used in the preparation of pharmaceutical compositions may be either organic or inorganic, solid or liquid in nature. Suitable solid excipients include gelatin, microcrystalline cellulose, lactose, starches, and magnesium strearate. Suitable liquid excipients include water and alcohols such as ethanol, benzyl alcohol and polyethylene glycol. The preferred liquid excipients for injectable preparations include water, saline solution, dextrose solution and glycol solutions such as aqueous propylene glycol or aqueous polyethylene glycol. The properties of the formulations may be enhanced by the addition of one or more adjuvants possessing properties as viscosity enhancers, surfactants, pH modifiers, preservatives, sweeteners, stability enhancers, coloring agents, suspending agents, granulating agents, coating agents, disintegration modifiers, propellants, emulsifying agents and humectants.

We claim:

1. A compound having the formula:

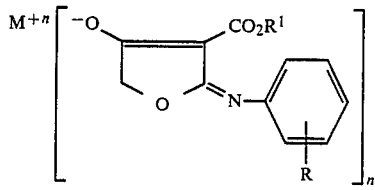

where;

n=1 or 2, M is an alkali or alkaline earth metal, R is hydrogen, lower alkyl, lower alkoxy, nitro, halogen or acetyl, and $R^1$ is lower alkyl.

2. The compound of claim 1 wherein the compound is potassium 2,5-dihydro-3-ethoxycarbonyl-2-(phenylimino)-4-furanyloxide.

3. The compound of claim 1 wherein the compound is potassium 2,5-dihydro-3-ethoxycarbony-2-[(3-methylphenyl)imino]-4-furanyloxide.

4. The compound of claim 1 wherein the compound is potassium 2,5-dihydro-3-ethoxycarbonyl-2-[(4-acetylphenyl)imino]-4-furanyloxide.

5. The compound of claim 1 wherein the compound is potassium 2,5-dihydro-3-ethoxycarbonyl-2-[(3-nitrophenyl)imino]-4-furanyloxide.

6. The compound of claim 1 wherein the compound is potassium 2,5-dihydro-3-ethoxycarbonyl-2-[(2-methoxyphenyl)imino]-4-furanyloxide.

7. The compound of claim 1 wherein the compound is potassium 2,5-dihydro-3-ethoxycarbonyl-2-[4-(bromophenyl)imino]-4-furanyloxide.

* * * * *